(12) United States Patent
Trieu et al.

(10) Patent No.: US 7,713,303 B2
(45) Date of Patent: *May 11, 2010

(54) COLLAGEN-BASED MATERIALS AND METHODS FOR AUGMENTING INTERVERTEBRAL DISCS

(75) Inventors: Hai H. Trieu, Cordova, TN (US); Michael C. Sherman, Memphis, TN (US)

(73) Assignee: Warsaw Orthopedic, Inc.

( * ) Notice: Subject to any disclaimer, the term of this patent is extended or adjusted under 35 U.S.C. 154(b) by 425 days.

This patent is subject to a terminal disclaimer.

(21) Appl. No.: 11/117,025

(22) Filed: Apr. 28, 2005

(65) Prior Publication Data

US 2005/0197707 A1  Sep. 8, 2005

Related U.S. Application Data

(63) Continuation of application No. 10/245,955, filed on Sep. 18, 2002, now abandoned.

(51) Int. Cl.
*A61F 2/44* (2006.01)
(52) U.S. Cl. .................................. 623/17.16
(58) Field of Classification Search ............ 623/17.16, 623/23.52, 23.58, 23.62, 23.63, 908, 919, 623/923
See application file for complete search history.

(56) References Cited

U.S. PATENT DOCUMENTS

| | | |
|---|---|---|
| 3,551,560 A | 12/1970 | Thiele |
| 3,855,638 A | 12/1974 | Pilliar |
| 3,875,595 A | 4/1975 | Froning |
| 4,060,081 A | 11/1977 | Yannas et al. |
| 4,085,466 A | 4/1978 | Goodfellow et al. |
| 4,185,813 A | 1/1980 | Spann |
| 4,280,954 A | 7/1981 | Yannas et al. |
| 4,344,193 A | 8/1982 | Kenny |
| 4,349,921 A | 9/1982 | Kuntz |
| 4,350,629 A | 9/1982 | Yannas et al. |
| 4,378,224 A | 3/1983 | Nimni et al. |
| 4,400,833 A | 8/1983 | Kurland |
| 4,418,691 A | 12/1983 | Yannas et al. |
| 4,424,208 A | 1/1984 | Wallace et al. |
| 4,448,718 A | 5/1984 | Yannas et al. |
| 4,458,678 A | 7/1984 | Yannas et al. |
| 4,505,266 A | 3/1985 | Yannas et al. |
| 4,544,516 A | 10/1985 | Hughes et al. |

(Continued)

FOREIGN PATENT DOCUMENTS

DE        19959975 A1     7/2001

(Continued)

OTHER PUBLICATIONS

Fascian—Printout from website: fascian.com.

(Continued)

*Primary Examiner*—Pedro Philogene

(57) ABSTRACT

A method of augmenting an intervertebral disc by injecting particles of collagen-based material into the disc. The particles may be dehydrated before implantation, and rehydrated after implantation, or they may be implanted in a "wet" state—such as a slurry or gel. Radiocontrast materials may be included to enhance imaging of the injected material. Other additives may include analgesics, antibiotics, proteoglycans, growth factors, and/or other cells effective to promote healing and/or proper disc function.

17 Claims, 6 Drawing Sheets

U.S. PATENT DOCUMENTS

| | | |
|---|---|---|
| 4,578,079 A | 3/1986 | Ruoslahti et al. |
| 4,582,640 A | 4/1986 | Smestad et al. |
| 4,589,881 A | 5/1986 | Pierschbacher et al. |
| 4,614,794 A | 9/1986 | Easton et al. |
| 4,627,853 A | 12/1986 | Campbell et al. |
| 4,642,117 A | 2/1987 | Nguyen et al. |
| 4,642,120 A | 2/1987 | Nevo et al. |
| 4,661,111 A | 4/1987 | Ruoslahti et al. |
| 4,703,108 A * | 10/1987 | Silver et al. .................. 530/356 |
| 4,772,287 A | 9/1988 | Ray et al. |
| 4,787,900 A | 11/1988 | Yannas |
| 4,801,299 A | 1/1989 | Brendel et al. |
| 4,803,075 A | 2/1989 | Wallace et al. |
| 4,837,285 A | 6/1989 | Berg et al. |
| 4,879,135 A | 11/1989 | Greco et al. |
| 4,880,492 A | 11/1989 | Erdmann et al. |
| 4,904,260 A | 2/1990 | Ray et al. |
| 4,946,792 A | 8/1990 | O'Leary |
| 4,976,733 A | 12/1990 | Giradot |
| 5,007,934 A | 4/1991 | Stone |
| 5,067,962 A | 11/1991 | Campbell et al. |
| 5,106,949 A * | 4/1992 | Kemp et al. .................. 530/356 |
| 5,108,438 A | 4/1992 | Stone |
| 5,137,514 A | 8/1992 | Ryan |
| 5,192,326 A * | 3/1993 | Bao et al. ................. 623/17.12 |
| 5,229,497 A | 7/1993 | Boni |
| 5,258,043 A | 11/1993 | Stone |
| 5,397,352 A | 3/1995 | Burres |
| 5,478,739 A | 12/1995 | Slivka et al. |
| 5,507,810 A | 4/1996 | Prewett et al. |
| 5,549,679 A | 8/1996 | Kuslich |
| 5,562,736 A | 10/1996 | Boyd et al. |
| 5,571,189 A | 11/1996 | Kuslich |
| 5,607,476 A | 3/1997 | Prewett et al. |
| 5,713,959 A | 2/1998 | Bartlett et al. |
| 5,733,337 A | 3/1998 | Carr, Jr. et al. |
| 5,788,625 A | 8/1998 | Plouhar et al. |
| 5,827,289 A | 10/1998 | Reiley et al. |
| 5,858,747 A | 1/1999 | Schinstine et al. |
| 5,888,220 A | 3/1999 | Felt et al. |
| 5,894,070 A | 4/1999 | Hansson et al. |
| 5,916,870 A | 6/1999 | Lee et al. |
| 5,922,028 A | 7/1999 | Plouhar et al. |
| 5,935,849 A | 8/1999 | Schinstine et al. |
| 5,948,428 A | 9/1999 | Lee et al. |
| 5,964,807 A | 10/1999 | Gan et al. |
| 5,976,186 A | 11/1999 | Bao et al. |
| 5,980,504 A | 11/1999 | Sharkey et al. |
| 5,994,325 A | 11/1999 | Roufa et al. |
| 6,007,570 A | 12/1999 | Sharkey et al. |
| 6,022,376 A | 2/2000 | Assell et al. |
| 6,025,538 A | 2/2000 | Yaccarino, III |
| 6,027,743 A | 2/2000 | Khouri et al. |
| 6,046,379 A | 4/2000 | Stone et al. |
| 6,066,154 A | 5/2000 | Reiley et al. |
| 6,073,051 A | 6/2000 | Sharkey et al. |
| 6,077,989 A | 6/2000 | Kandel et al. |
| 6,080,194 A | 6/2000 | Pachence et al. |
| 6,080,579 A | 6/2000 | Hanley, Jr. et al. |
| 6,095,149 A | 8/2000 | Sharkey et al. |
| 6,099,514 A | 8/2000 | Sharkey et al. |
| 6,122,549 A | 9/2000 | Sharkey et al. |
| 6,123,731 A | 9/2000 | Boyce et al. |
| 6,126,682 A | 10/2000 | Sharkey et al. |
| 6,140,452 A | 10/2000 | Felt et al. |
| 6,146,422 A | 11/2000 | Lawson |
| 6,165,489 A | 12/2000 | Berg et al. |
| 6,176,880 B1 | 1/2001 | Plouhar et al. |
| 6,179,872 B1 | 1/2001 | Bell et al. |
| 6,197,061 B1 | 3/2001 | Masuda et al. |
| 6,224,630 B1 | 5/2001 | Bao et al. |
| 6,235,043 B1 | 5/2001 | Reiley et al. |
| 6,240,926 B1 * | 6/2001 | Chin Gan et al. ........... 128/898 |
| 6,248,110 B1 | 6/2001 | Reiley et al. |
| 6,248,131 B1 | 6/2001 | Felt et al. |
| 6,261,311 B1 | 7/2001 | Sharkey et al. |
| 6,264,659 B1 | 7/2001 | Ross et al. |
| 6,264,695 B1 | 7/2001 | Stoy |
| 6,290,715 B1 | 9/2001 | Sharkey et al. |
| 6,306,169 B1 | 10/2001 | Lee et al. |
| 6,306,177 B1 | 10/2001 | Felt et al. |
| 6,322,786 B1 | 11/2001 | Anderson |
| 6,324,710 B1 | 12/2001 | Hernandez et al. |
| 6,340,369 B1 | 1/2002 | Ferree |
| 6,344,058 B1 * | 2/2002 | Ferree ..................... 623/17.11 |
| 6,352,557 B1 | 3/2002 | Ferree |
| 6,352,558 B1 | 3/2002 | Spector |
| 6,402,784 B1 | 6/2002 | Wardlaw |
| 6,419,702 B1 | 7/2002 | Ferree |
| 6,423,083 B2 | 7/2002 | Reiley et al. |
| 6,425,919 B1 | 7/2002 | Lambrecht |
| 6,428,576 B1 | 8/2002 | Haldimann |
| 6,436,119 B1 | 8/2002 | Erb et al. |
| 6,443,988 B2 | 9/2002 | Felt et al. |
| 6,482,235 B1 | 11/2002 | Lambrecht et al. |
| 6,592,625 B2 * | 7/2003 | Cauthen .................. 623/17.16 |
| 6,623,963 B1 | 9/2003 | Muller et al. |
| 6,641,587 B2 | 11/2003 | Scribner et al. |
| 6,648,918 B2 | 11/2003 | Ferree |
| 6,662,805 B2 | 12/2003 | Frondoza et al. |
| 6,699,294 B2 | 3/2004 | Urry |
| 6,712,853 B2 | 3/2004 | Kuslich |
| 6,716,251 B1 | 4/2004 | Asius et al. |
| 6,723,335 B1 | 4/2004 | Moehlenbruck et al. |
| 6,726,691 B2 | 4/2004 | Osorio et al. |
| 6,783,546 B2 | 8/2004 | Zucherman et al. |
| 6,793,677 B2 | 9/2004 | Ferree |
| 6,827,716 B2 | 12/2004 | Ryan et al. |
| 6,929,640 B1 | 8/2005 | Underwood et al. |
| 6,932,843 B2 | 8/2005 | Smith et al. |
| 6,936,072 B2 | 8/2005 | Lambrecht et al. |
| 6,939,329 B1 | 9/2005 | Verkaart |
| 6,958,077 B2 | 10/2005 | Suddaby |
| 6,969,404 B2 | 11/2005 | Ferree |
| 6,980,862 B2 | 12/2005 | Fredricks et al. |
| 7,001,431 B2 | 2/2006 | Bao et al. |
| 7,060,103 B2 | 6/2006 | Carr, Jr. et al. |
| 7,077,865 B2 | 7/2006 | Bao et al. |
| 2001/0004710 A1 | 6/2001 | Felt et al. |
| 2001/0006948 A1 | 7/2001 | Kang et al. |
| 2001/0011174 A1 | 8/2001 | Reiley et al. |
| 2001/0016195 A1 | 8/2001 | Tobinick |
| 2001/0016772 A1 | 8/2001 | Lee et al. |
| 2001/0020476 A1 | 9/2001 | Gan et al. |
| 2001/0024823 A1 | 9/2001 | Vukicevic et al. |
| 2001/0027199 A1 | 10/2001 | Olmarker |
| 2001/0049527 A1 | 12/2001 | Cragg |
| 2001/0049531 A1 | 12/2001 | Reiley et al. |
| 2001/0051834 A1 | 12/2001 | Frondoza et al. |
| 2001/0055594 A1 | 12/2001 | Olmarker et al. |
| 2002/0016583 A1 | 2/2002 | Cragg |
| 2002/0026195 A1 | 2/2002 | Layne et al. |
| 2002/0029083 A1 | 3/2002 | Zucherman et al. |
| 2002/0032155 A1 | 3/2002 | Ferree |
| 2002/0038150 A1 | 3/2002 | Urry |
| 2002/0045942 A1 | 4/2002 | Ham |
| 2002/0049498 A1 | 4/2002 | Yuksel et al. |
| 2002/0055143 A1 | 5/2002 | Bell et al. |
| 2002/0068974 A1 | 6/2002 | Kuslich et al. |
| 2002/0068975 A1 | 6/2002 | Teitelbaum et al. |
| 2002/0082608 A1 | 6/2002 | Reiley et al. |
| 2002/0115742 A1 | 8/2002 | Trieu et al. |
| 2002/0116069 A1 | 8/2002 | Urry |
| 2002/0120347 A1 | 8/2002 | Boyer II et al. |

| | | |
|---|---|---|
| 2002/0133231 A1 | 9/2002 | Ferree |
| 2002/0151979 A1 | 10/2002 | Lambrecht et al. |
| 2002/0176893 A1 | 11/2002 | Wironen et al. |
| 2002/0177866 A1 | 11/2002 | Weikel et al. |
| 2003/0008817 A1 | 1/2003 | Sander |
| 2003/0104026 A1 | 6/2003 | Wironen et al. |
| 2003/0130664 A1 | 7/2003 | Boucher et al. |
| 2003/0158607 A1* | 8/2003 | Carr et al. ................ 623/23.72 |
| 2004/0010251 A1 | 1/2004 | Pitaru et al. |
| 2004/0024081 A1 | 2/2004 | Trieu et al. |
| 2004/0030392 A1 | 2/2004 | Lambrecht et al. |
| 2004/0034429 A1 | 2/2004 | Lambrecht et al. |
| 2004/0054414 A1 | 3/2004 | Trieu et al. |
| 2004/0064023 A1 | 4/2004 | Ryan et al. |
| 2004/0073308 A1 | 4/2004 | Kuslich et al. |
| 2004/0083001 A1 | 4/2004 | Kandel |
| 2004/0083002 A1 | 4/2004 | Belef et al. |
| 2004/0091540 A1 | 5/2004 | Desrosier et al. |
| 2004/0092946 A1 | 5/2004 | Bagga et al. |
| 2004/0101959 A1 | 5/2004 | Marko et al. |
| 2004/0172132 A1 | 9/2004 | Ginn |
| 2004/0186471 A1 | 9/2004 | Trieu |
| 2004/0220101 A1 | 11/2004 | Ferree |
| 2004/0220102 A1 | 11/2004 | Ferree |
| 2004/0228901 A1 | 11/2004 | Trieu et al. |
| 2004/0229786 A1 | 11/2004 | Attawia et al. |
| 2004/0260397 A1 | 12/2004 | Lambrecht et al. |
| 2005/0002909 A1 | 1/2005 | Moehlenbruck et al. |
| 2005/0055094 A1 | 3/2005 | Kuslich |
| 2005/0069571 A1 | 3/2005 | Slivka et al. |
| 2005/0070915 A1 | 3/2005 | Mazzuca et al. |
| 2005/0090901 A1 | 4/2005 | Studer |
| 2005/0100538 A1 | 5/2005 | Mohamed et al. |
| 2005/0102030 A1 | 5/2005 | Yuksel et al. |
| 2005/0113923 A1 | 5/2005 | Acker et al. |
| 2005/0118228 A1 | 6/2005 | Trieu et al. |
| 2005/0119750 A1 | 6/2005 | Studer |
| 2005/0119754 A1 | 6/2005 | Trieu et al. |
| 2005/0125066 A1 | 6/2005 | McAfee |
| 2005/0131540 A1 | 6/2005 | Trieu |
| 2005/0131541 A1 | 6/2005 | Trieu |
| 2005/0143688 A1 | 6/2005 | Lin et al. |
| 2005/0149007 A1 | 7/2005 | Carl |
| 2005/0149046 A1 | 7/2005 | Friedman et al. |
| 2005/0149197 A1* | 7/2005 | Cauthen .................. 623/17.16 |
| 2005/0152986 A1 | 7/2005 | Duneas et al. |
| 2005/0154463 A1 | 7/2005 | Trieu |
| 2005/0159817 A1 | 7/2005 | Ferree |
| 2005/0177168 A1 | 8/2005 | Brunnett et al. |
| 2005/0182414 A1 | 8/2005 | Manzi et al. |
| 2005/0182418 A1 | 8/2005 | Boyd et al. |
| 2005/0186673 A1 | 8/2005 | Geistlich et al. |
| 2005/0187543 A1 | 8/2005 | Underwood et al. |
| 2005/0187556 A1 | 8/2005 | Stack et al. |
| 2005/0191331 A1 | 9/2005 | Hunter et al. |
| 2005/0196387 A1 | 9/2005 | Seyedin et al. |
| 2005/0197707 A1 | 9/2005 | Trieu |
| 2005/0203206 A1 | 9/2005 | Trieu |
| 2005/0203527 A1 | 9/2005 | Carrison et al. |
| 2005/0203537 A1 | 9/2005 | Wiley et al. |
| 2005/0209595 A1 | 9/2005 | Karmon |
| 2005/0209601 A1 | 9/2005 | Bowman et al. |
| 2005/0209602 A1 | 9/2005 | Bowman et al. |
| 2005/0222538 A1 | 10/2005 | Embry et al. |
| 2005/0222684 A1 | 10/2005 | Ferree |
| 2005/0234493 A1 | 10/2005 | Carr et al. |
| 2005/0234498 A1 | 10/2005 | Gronemeyer et al. |
| 2005/0234557 A1 | 10/2005 | Lambrecht et al. |
| 2005/0240171 A1 | 10/2005 | Forrest |
| 2005/0251259 A1 | 11/2005 | Suddaby |
| 2005/0256580 A1 | 11/2005 | Marissen |
| 2005/0261684 A1 | 11/2005 | Shaolian et al. |
| 2005/0267580 A1 | 12/2005 | Suddaby |
| 2005/0267583 A1 | 12/2005 | Higham et al. |
| 2005/0273093 A1 | 12/2005 | Patel et al. |
| 2005/0277996 A1 | 12/2005 | Podhajsky |
| 2006/0019869 A1 | 1/2006 | Thomas et al. |
| 2006/0044561 A1 | 3/2006 | Nii |
| 2006/0196387 A1 | 9/2006 | Hartley et al. |
| 2007/0026053 A1 | 2/2007 | Pedrozo et al. |

FOREIGN PATENT DOCUMENTS

| | | |
|---|---|---|
| EP | 00305026 | 3/1988 |
| EP | 00277678 | 10/1988 |
| EP | 0747067 A2 | 12/1996 |
| EP | 1313412 A2 | 5/2003 |
| EP | 1407729 A1 | 4/2004 |
| EP | 1421957 A1 | 5/2004 |
| EP | 1328222 B1 | 3/2005 |
| EP | 1214026 B1 | 4/2005 |
| EP | 1198209 B1 | 5/2005 |
| EP | 1582166 A2 | 5/2005 |
| EP | 1051207 B1 | 8/2005 |
| EP | 1563808 A1 | 8/2005 |
| EP | 1563809 A2 | 8/2005 |
| EP | 15754548 A1 | 9/2005 |
| GB | 01515963 | 6/1978 |
| GB | 2407580 A | 5/2005 |
| JP | 2005103296 A | 4/2005 |
| JP | 2005118436 A | 5/2005 |
| JP | 2005152501 A | 6/2005 |
| WO | WO8910728 | 11/1989 |
| WO | 99/04720 A1 | 2/1992 |
| WO | 9210982 A1 | 7/1992 |
| WO | 9611642 A1 | 4/1996 |
| WO | 97/22371 A1 | 6/1997 |
| WO | WO 99/02108 * | 1/1999 |
| WO | 99/43271 | 9/1999 |
| WO | 9959669 A1 | 11/1999 |
| WO | 9961084 A1 | 12/1999 |
| WO | 9962439 | 12/1999 |
| WO | 0034556 A1 | 6/2000 |
| WO | 00/62832 A1 | 10/2000 |
| WO | 00/75659 A1 | 12/2000 |
| WO | 01/76654 A1 | 10/2001 |
| WO | 0217825 A2 | 3/2002 |
| WO | 02/40070 A2 | 5/2002 |
| WO | 02/054978 A2 | 7/2002 |
| WO | 02/000142 A2 | 10/2002 |
| WO | 03011155 A2 | 2/2003 |
| WO | 03066120 A1 | 8/2003 |
| WO | 03099230 A2 | 12/2003 |
| WO | 2004002375 A1 | 1/2004 |
| WO | 2004022155 A2 | 3/2004 |
| WO | 2004/026189 A2 | 4/2004 |
| WO | 2004026190 A2 | 4/2004 |
| WO | 2004028414 A1 | 4/2004 |
| WO | 2004030548 A1 | 4/2004 |
| WO | 2004032808 A2 | 4/2004 |
| WO | 2004041075 A2 | 5/2004 |
| WO | 2004/045667 A1 | 6/2004 |
| WO | 2004060425 A2 | 7/2004 |
| WO | 2004064673 A2 | 8/2004 |
| WO | 2004069296 A1 | 8/2004 |
| WO | 2004073532 A1 | 9/2004 |
| WO | 2004073563 A2 | 9/2004 |
| WO | 2004/093934 A2 | 11/2004 |
| WO | 2005000283 A2 | 1/2005 |
| WO | 2005004755 A1 | 1/2005 |
| WO | 2005032434 A1 | 4/2005 |
| WO | 2005034781 A1 | 4/2005 |
| WO | 2005034800 A2 | 4/2005 |
| WO | 2005041813 A2 | 5/2005 |
| WO | 2005049055 A1 | 6/2005 |
| WO | 2005063316 A1 | 7/2005 |

| | | | |
|---|---|---|---|
| WO | 2005070071 A2 | 8/2005 | |
| WO | 2005070439 A1 | 8/2005 | |
| WO | 2005081870 A2 | 9/2005 | |
| WO | 2005092248 A1 | 10/2005 | |
| WO | 2005092249 A1 | 10/2005 | |
| WO | 2005096978 A1 | 10/2005 | |
| WO | 2005099392 A2 | 10/2005 | |
| WO | 2005102433 A2 | 11/2005 | |
| WO | 2005102440 A2 | 11/2005 | |
| WO | 2005105168 A1 | 11/2005 | |
| WO | 2005107827 A1 | 11/2005 | |
| WO | 2005113032 A2 | 12/2005 | |
| WO | 2005118015 A1 | 12/2005 | |
| WO | 2006002417 A2 | 1/2006 | |
| WO | 2006138098 A1 | 12/2006 | |

OTHER PUBLICATIONS

Tay, B.K., et al., "Use of a Collagen-Hydroxyapatite Matrix in Spinal Fusion. A Rabbit Model," SPINE, vol. 23, No. 21, pp. 2276-2281, Nov. 1, 1998.

Burres, S., "Fascian," Facial Plast Surg, vol. 20, No. 2, pp. 149-152, May 2004.

Burres, S., "Midface Volume Replacement with a Transmaxiallary Implant," Aesthetic Plast Surg, vol. 29, No. 1, pp. 1-4, Jan.-Feb. 2005.

Burres, S., "Soft-tissue augmentation with fascian," Clin Plast Surg, vol. 28, No. 1, pp. 101-110, Jan. 2001. Abstract Only.

Burres, S., "Preserved Participate Fascia Lata for Injection: A New Alternative," vol. 25, No. 10, pp. 790-794, Oct. 1999.

Burres, S., "Intralingual Injection of Particulate Fascia for Tongue Paralysis," Rhinological and Otological Society, Inc., The Laryngoscope, vol. 114, pp. 1204-1205, Jul. 2004.

Shore, J. W., "Injectable Lyophilized Particulate Human Fascia Lata (Fascian) for Lip, Perioral, and Glabellar Enhancement," Ophthalmic Plastic and Reconstructive Surgery, vol. 16, No. 1, pp. 23-27, Jan. 2000.

* cited by examiner

COLLAGEN-BASED MATERIALS AND METHODS FOR AUGMENTING INTERVERTEBRAL DISCS

REFERENCE TO RELATED APPLICATION

This application is a continuation and claims priority from U.S. patent application Ser. No. 10/245,955, filed Sep. 18, 2002, now abandoned, which is incorporated herein by reference in its entirety.

FIELD OF THE INVENTION

The present invention relates generally to materials and methods for augmenting intervertebral discs, and more particularly to materials and methods for augmenting intervertebral discs with collagen-based materials.

BACKGROUND OF THE INVENTION

A healthy intervertebral disc facilitates motion between pairs of vertebrae while absorbing and distributing shocks. The disc is composed of two parts: a soft central core (the nucleus pulposus) that bears the majority of the load, and a tough outer ring (the annulus fibrosis) that holds and stabilizes the core material.

As the natural aging process progresses, the disc may dehydrate and degenerate, adversely affecting its ability to adequately cushion and support the vertebral bodies. This natural desiccation, which in its more advanced state is often referred to as "black disc" because of the disc's dehydrated appearance on Magnetic Resonance Imaging [MRI], can cause discomfort to the patient as the vertebrae to come closer together—compressing the spinal nerves and causing pain.

Techniques for addressing degenerative disc disease have heretofore relied primarily on disc replacement methods. In cases in which a dehydrated and/or degenerating disc was augmented before disc replacement was required, the augmentation materials have primarily been synthetic devices that expand, are inflated, or deploy expanding elements when implanted into the disc.

A need therefore exists for materials and methods effective for augmenting intervertebral discs with natural materials. The present invention addresses that need.

SUMMARY OF THE INVENTION

Briefly describing one aspect of the present invention, there is provided a method of augmenting an intervertebral disc by injecting particles of collagen-based material into the disc. The particles may be implanted in a dehydrated form, and rehydrated after implantation, or they may be implanted in a hydrated form, such as a slurry or gel. Cross-linking agents such as glutaraldehyde may be included in the injected material to promote collagen crosslinking. In addition, radio-contrast materials may be included to enhance imaging of the injected material. Similarly, performance-enhancing additives such as analgesics and/or antibiotics may be included to provide additional therapeutic benefits.

Objects and advantages of the claimed invention will be apparent from the following description.

DESCRIPTION OF THE PREFERRED EMBODIMENTS

Figure 1A:
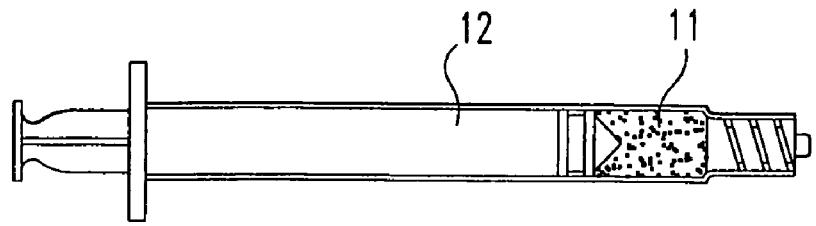
FIGS. 1A-1D show a procedure for injecting a collagen-based material into an intervertebral disc, according to one preferred embodiment of the present invention.

For the purposes of promoting an understanding of the principles of the invention, reference will now be made to certain preferred embodiments and specific language will be used to describe the same. It will nevertheless be understood that no limitation of the scope of the invention is thereby intended, such alterations and further modifications in the preferred embodiments being contemplated as would normally occur to one skilled in the art to which the invention relates.

As indicated above, one aspect of the present invention relates to materials and methods for using collagen-based material to augment an intervertebral disc. In the most preferred embodiments the collagen-based material is injected into a disc nucleus that is contained in a substantially sound annulus. In other embodiments the collagen-based material is injected into a disc nucleus that is contained in a damaged or defective annulus.

The collagen-based material is preferably derived from natural, collagen-rich tissue, such as intervertebral disc, fascia, ligament, tendon, demineralized bone matrix, etc. The material may be autogenic, allogenic, or xenogenic, or it may be of human-recombinant origin. In alternative embodiments the collagen-based material may be a synthetic, collagen-based material. Examples of preferred collagen-rich tissues include disc annulus, fascia lata, planar fascia, anterior or posterior cruciate ligaments, patella tendon, hamstring tendons, quadriceps tendons, Achilles tendons, skins, and other connective tissues.

The collagen-based material may be provided in any form appropriate for introduction into a disc space. For example, the material may be a solid, porous, woven, or non-woven material. The material may be provided as particles or small pieces, or as a fibrous material.

In some embodiments the material is provided in a dehydrated state, and is "rehydrated" after implantation in the disc. In other embodiments the material is implanted "wet." When the material is "wet," it may be that way because it has never been dehydrated, or it may have been dehydrated and reconstituted. When reconstituted, the material may be reconstituted with saline or another aqueous medium, or it may be reconstituted with a non-aqueous medium such as ethylene glycol or another alcohol. Moreover, when provided in a "wet" state, the material may be provided as a gel, solution, suspension, dispersion, emulsion, paste, etc.

In the most preferred embodiments the material is a particulate and/or fibrous material suitable for injection through a hypodermic needle into a disc.

In the most preferred embodiments the collagen material is provided as particles ranging between 0.05 mm and 5 mm in size. When materials such as fascia lata or disc annulus particles are used the particles preferably range in size from 0.1 mm to 5 mm. When materials such as demineralized bone matrix are used the particles preferably range in size from 0.05 mm to 3 mm. When small plugs of material are used the plugs preferably range in size from 0.5 mm to 5 mm. In some embodiments larger sized pieces, such as pieces up to 20 mm in size, may be used.

The materials may be processed or fabricated using more than one type of tissue. For example, mixtures of fascia lata and demineralized bone matrix may be preferred in appropriate cases, as may mixtures of DBM and annulus fibrosis material.

Cross-linking agents may be added to the formulation to promote cross-linking of the collagen material. For example, glutaraldehyde or other protein cross-linking agents may be included in the formulation. The cross-linking agents may promote covalent or non-covalent crosslinks between collagen molecules. Similarly, agents to inhibit protein denaturization may also be included. Crosslinking agents that would be appropriate for use in the claimed invention are known to persons skilled in the art, and may be selected without undue experimentation.

When the material is to be used as a slurry or gel, additives to promote slurry or gel formation may also be included. These additives may promote protein folding, water binding, protein-protein interactions, and water immobilization.

In addition, a radiocontrast media, such as barium sulfate, or a radiocontrast dye, such as HYPAQUE®, may be included to aid the surgeon in tracking the movement and/or location of the injected material. Radiocontrast materials appropriate for use in discography are known to persons skilled in the art, and may be selected for use in the present invention without undue experimentation.

Finally, other additives to provide benefits to the injected collagen-based material may also be included. Such additives include anesthetics, to reduce pain caused by the procedure, and antibiotics, to minimize the potential for bacterial infection.

Proteoglycans may also be included to attract and/or bind water to keep the nucleus hydrated. Similarly, growth factors and/or other cells (e.g., intervertebral disc cells, stem cells, etc.) to promote healing, repair, regeneration and/or restoration of the disc, and/or to facilitate proper disc function, may also be included. Additives appropriate for use in the claimed invention are known to persons skilled in the art, and may be selected without undue experimentation.

In some embodiments the collagen material is dehydrated before injection into the disc space, where it is rehydrated by absorbing fluid from the disc space. In other embodiments the collagen material is provided as a gel, slurry, or other hydrated formulation before implantation.

The collagen-based material is "surgically added" to the disc space. That is, the material is added by the intervention of medical personnel, as distinguished from being "added" by the body's natural growth or regeneration processes. The surgical procedure preferably includes injection through a hypodermic needle, although other surgical methods of introducing the collagen-based material into the disc may be used. For example, the material may be introduced into a disc by extrusion through a dilated annular opening, infusion through a catheter, insertion through an opening created by trauma or surgical incision, or by other means of invasive or minimally invasive deposition of the materials into the disc space.

Figure 1B:
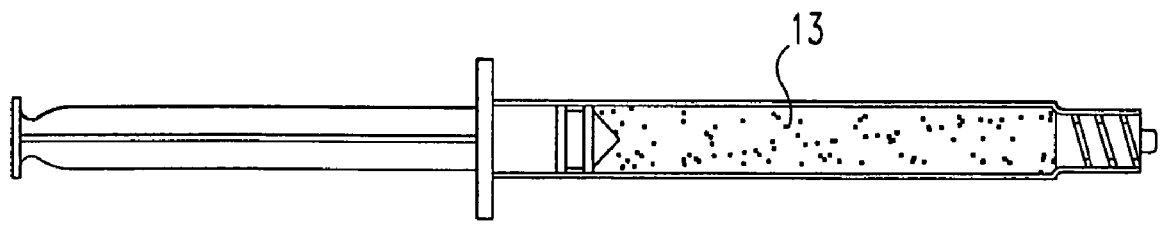
Figure 1C:
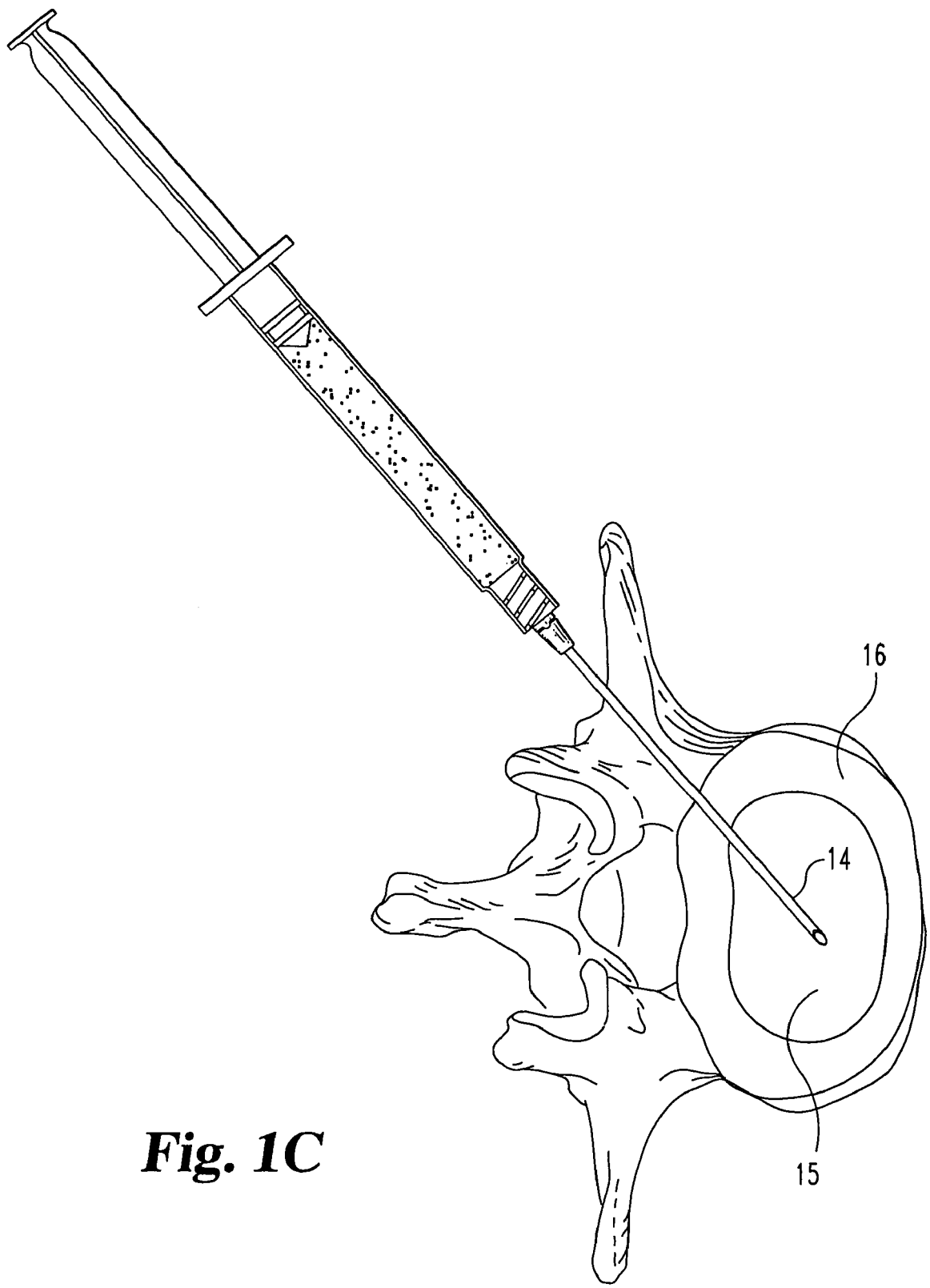
Figure 1D:
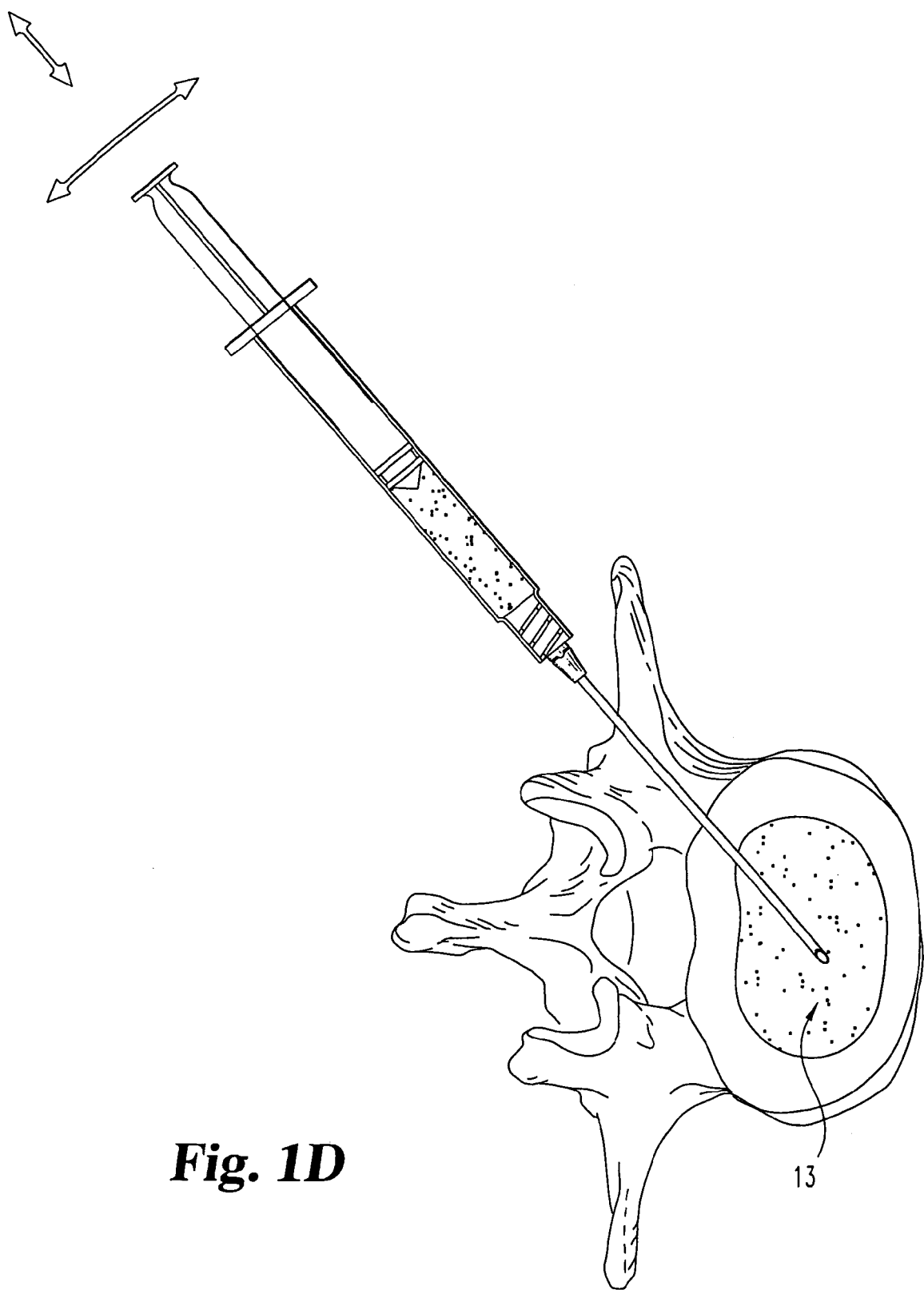

Referring now to the drawings, FIGS. 1A-1D show one method of injecting a collagen-based material into a disc. In FIG. 1A, dehydrated particulate fascia lata or annulus fibrosis material 11 is provided in a syringe 12 (in a sterile package). The material is rehydrated and/or dispersed in a suspension medium as shown in FIG. 1B, to provide a wet dispersion 13 of collagen-based material. A hypodermic needle 14 is attached to syringe 12, and the syringe is inserted into a nucleus pulposus 15 contained within a disc annulus 16 (FIG. 1C). The needle/syringe may be moved around within the disc space, sweeping from side to side and back and forth, to ensure uniform distribution of the collagen-based material 13 within the disc space, as shown in FIG. 1D. It is preferred, however, that the tip of the needle be maintained near the center of the disc to ensure deposition of the material within the nuclear disc space, and to minimize potential leakage.

Figure 2A:
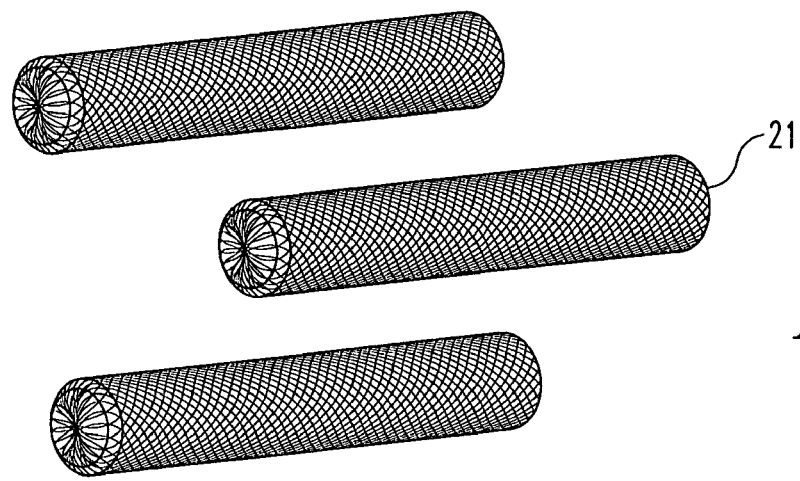
FIGS. 2A-2F show a procedure for injecting a collagen-based material into an intervertebral disc, according to another preferred embodiment of the present invention.
Figure 2B:
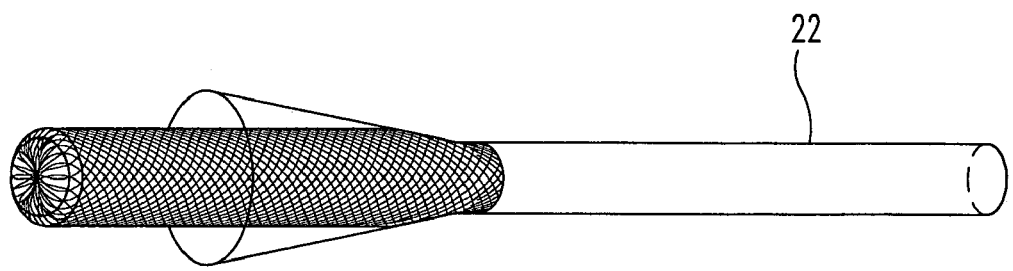
Figure 2C:

Alternatively, small collagen plugs 21 may be inserted into the disc space as shown in FIGS. 2A-2F. The collagen plugs 21 may be compressed before or by insertion into a small diameter tube 22, and are provided in a delivery cannula 23 (FIGS. 2A-2C). The delivery cannula 23 is attached to a dilator 24.

Figure 2D:
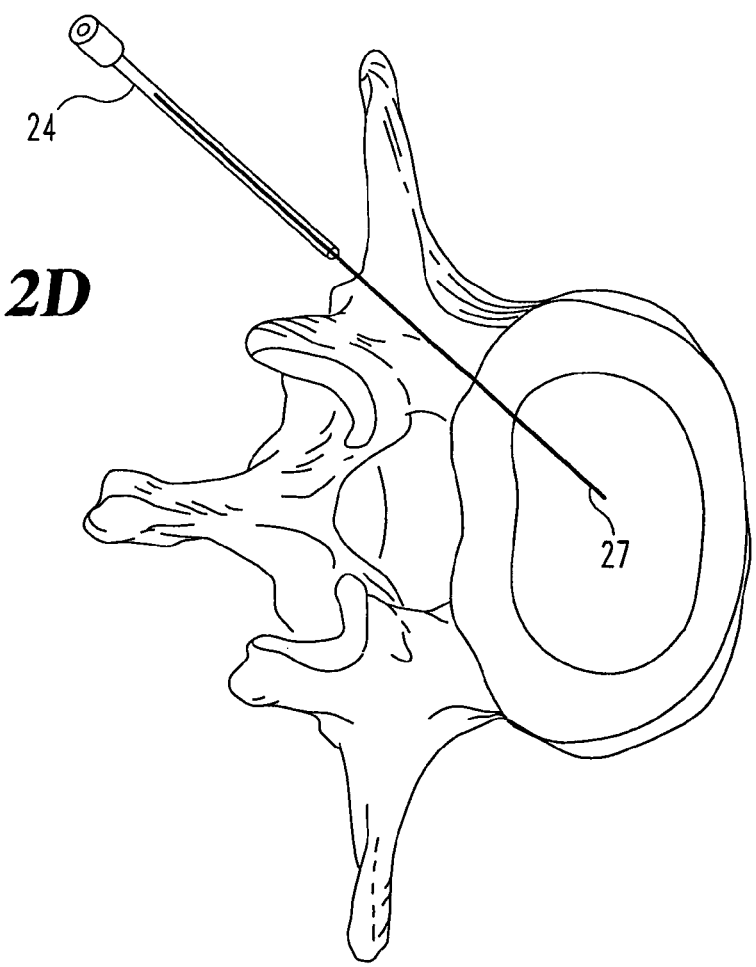
Figure 2E:
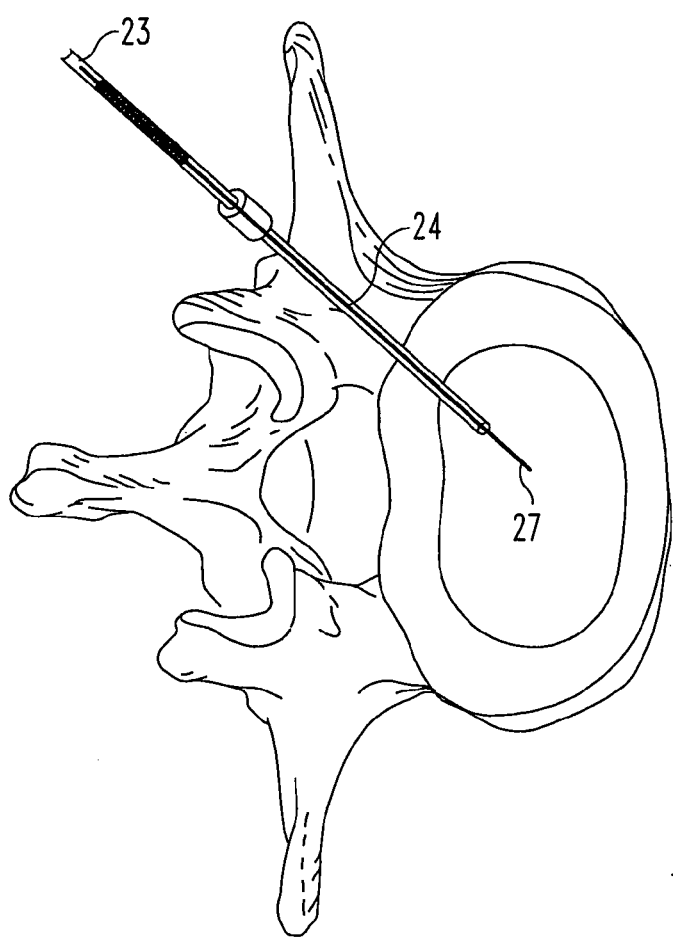
Figure 2F:
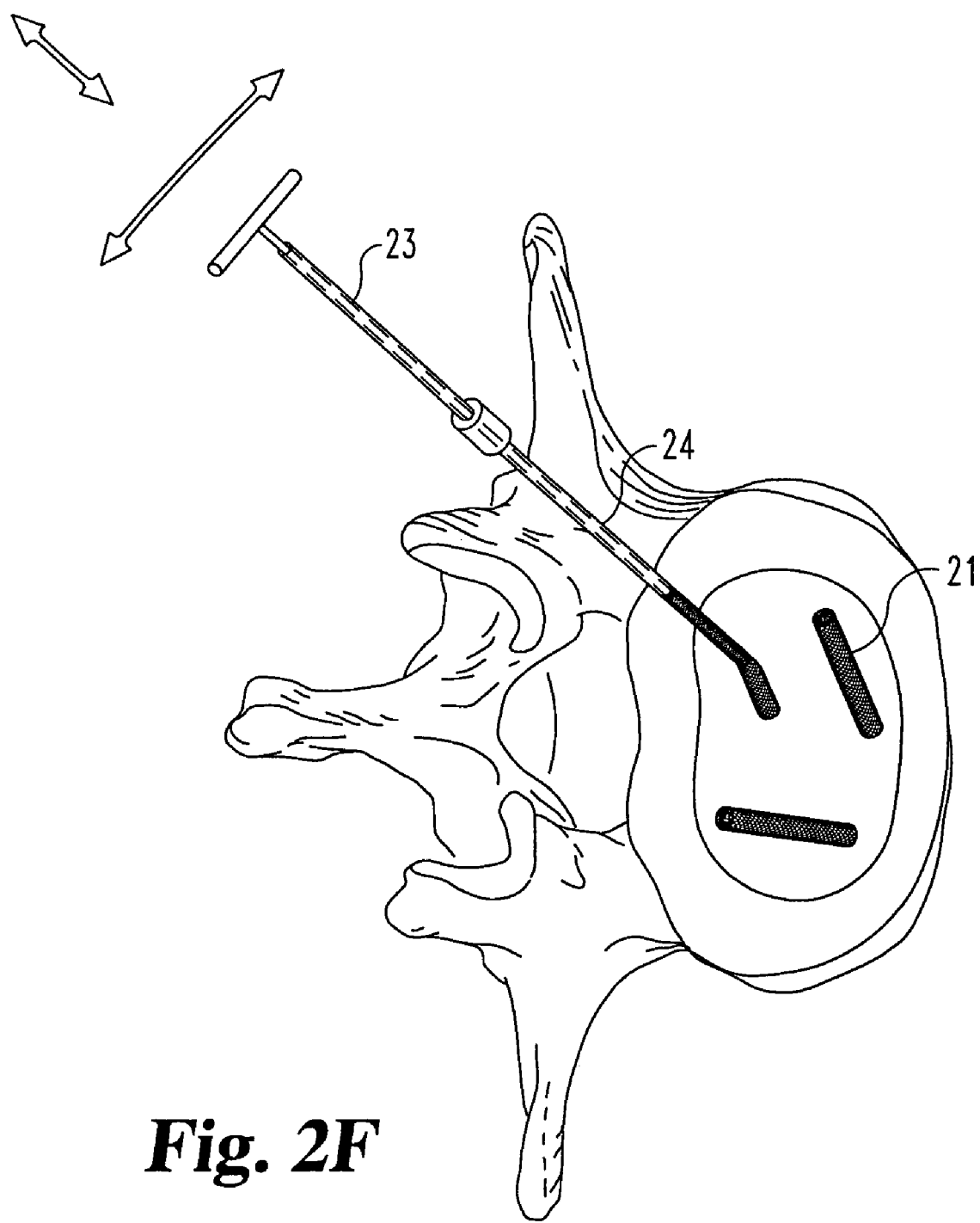

The compressed plugs are inserted into a disc nucleus 25 having a substantially intact annulus 26 by penetrating the annulus with a guide needle 27 (FIG. 2D). Dilator 24, preferably with delivery cannula 23 already attached, is inserted through the annulus over guide needle 27 (FIG. 2E). The collagen plugs 21 are then ready for injection (or extrusion) into the disc space.

The collagen plugs are deposited into the disc space. As with the wet particulate/fibrous material, the cannula may be moved up and back, and/or side to side, to ensure even distribution of the plugs (FIG. 2F) a plunger 28 may be used to push the plugs from the cannula.

The plugs expand upon exiting the dilator, and may further expand as they rehydrate in the disc space.

As to the benefits of the inventive materials and methods, augmentation of the intervertebral disc may restore or improve the natural condition and/or performance of the disc. In addition, augmentation may retard or reverse the progressive degeneration of a dehydrated disc.

Reference will now be made to specific examples using the processes described above. It is to be understood that the examples are provided to more completely describe preferred embodiments, and that no limitation to the scope of the invention is intended thereby.

EXAMPLE 1A

Hydrated Particulate Fascia Lata

A suspension of particulate or fibrous (autologous or allogenic) fascia lata is prepared in a biocompatible medium such as saline or ethylene glycol. The particle size ranges from 0.1 mm to 5 mm, with most particles being between 0.25 and 2 mm.

The suspension is injected directly into the nuclear disc space through an intact annulus using a hypodermic needle, and is contained within the disc space following injection. The medium subsequently diffuses out of the disc space and leaves the fascia lata material behind.

Inspection of the disc reveals that an appropriate level of augmentation may be obtained with a single injection of material. Alternatively, several smaller doses/injections may be used to achieve comparable results.

EXAMPLE 1B

Hydrated Particulate Fascia Lata with Crosslinking Agent

A suspension of particulate or fibrous (autologous or allogenic) fascia lata is prepared in a biocompatible medium such as saline or ethylene glycol. The particle size ranges from 0.1 mm to 5 mm, with most particles being between 0.25 mm and 2 mm. A glutaraldehyde crosslinking agent is added to promote collagen crosslinking.

The suspension is injected directly into the nuclear disc space through an intact annulus using a hypodermic needle, and is contained within the disc space following injection.

The medium subsequently diffuses out of the disc space and leaves the fascia lata material behind.

Inspection of the disc reveals that an appropriate level of augmentation may be obtained through either a single injection of material, or by multiple injections.

EXAMPLE 1C

Dehydrated Particulate Fascia Lata

Dehydrated fascia lata material is provided in particulate form. Particle sizes range between 0.05 mm and 3 mm, with most particles being between 0.10 mm and 1 mm. The dehydrated material is loaded in a specially designed syringe for delivery of solid materials.

The material is extruded into the nuclear disc space of the treated disc through a small dilated annular opening. The material remains inside the disc space after the needle is removed. It subsequently absorbs moisture or body fluids and swells up in vivo.

Inspection of the disc reveals that an appropriate level of augmentation may be obtained through either a single injection of material, or by multiple injections.

EXAMPLE 2A

Hydrated Particulate Disc Annulus Material

A suspension of particulate or fibrous allogenic annulus fibrosis is prepared in a biocompatible medium such as saline or ethylene glycol. The particle size ranges from 0.1 mm to 5 mm, with most particles being between 0.25 and 2 mm.

The suspension is injected directly into the nuclear disc space through an intact annulus using a hypodermic needle. The suspension is contained within the disc space following injection. The medium subsequently diffuses out of the disc space and leaves the annulus fibrosis material behind.

Inspection of the disc reveals that an appropriate level of augmentation may be obtained through either a single injection of material, or by multiple injections.

EXAMPLE 2B

Hydrated Particulate Disc Annulus Material with Crosslinking Agent

A suspension of particulate or fibrous allogenic annulus fibrosis is prepared in a biocompatible medium such as saline or ethylene glycol. The particle size ranges from 0.1 mm to 5 mm, with most particles being between 0.25 and 2 mm. A glutaraldehyde crosslinking agent is added to promote collagen crosslinking.

The suspension is injected directly into the nuclear disc space through an intact annulus using a hypodermic needle. The suspension is contained within the disc space following injection. The medium subsequently diffuses out of the disc space and leaves the annulus fibrosis material behind.

Inspection of the disc reveals that an appropriate level of augmentation may be obtained through either a single injection of material, or by multiple injections.

EXAMPLES 3A-3C

Dehydrated Annulus Fibrosis

Dehydrated annulus fibrosis is provided in granule, particulate and powder form, for example 3A-3C respectively. Particle sizes range between 0.05 mm and 3 mm, with most particles being between 0.10 mm and 1 mm. The dehydrated material is loaded in a specially designed syringe for delivery of solid materials.

The material is extruded into the nuclear disc space of the treated disc through a small dilated annular opening. The material remains inside the disc space after the needle is removed. It subsequently absorbs moisture or body fluids and swells up in vivo.

Inspection of the disc reveals that an appropriate level of augmentation may be obtained through either a single injection of material, or by multiple injections.

EXAMPLES 4A-4B

Demineralized Bone Matrix (DBM) Gel

Demineralized bone matrix (DBM) gel is provided with and without glutaraldehyde as a cross-linker additive (examples 4A and 4B, respectively). In both cases the material is warmed up to an appropriate temperature for melting or thinning out the gel, and is injected directly into the nuclear disc space through an intact annulus using a hypodermic needle. The DBM gel becomes solidified in the disc space after injection.

Inspection of the disc reveals that an appropriate level of augmentation may be obtained through either a single injection of material, or by multiple injections.

EXAMPLES 4C

Dehydrated Demineralized Bone Matrix (DBM)

Dehydrated DBM is provided in granule, particulate and powder form. Particle sizes range between 0.05 mm and 3 mm, with most particles being between 0.10 mm and 1 mm. The dehydrated material is loaded in a specially designed syringe for delivery of solid materials.

The material is extruded into the nuclear disc space of the treated disc through a small dilated annular opening. The material remains inside the disc space after the needle is removed. It subsequently absorbs moisture or body fluids and swells up in vivo.

Inspection of the disc reveals that an appropriate level of augmentation may be obtained through either a single injection of material, or by multiple injections.

EXAMPLE 5A-5D

Mixtures of Annulus Fibrosis and Demineralized Bone Matrix

Mixtures of particulate and fibrous allogenic annulus fibrosis and demineralized bone matrix (DBM) gel, with and without additives and/or cross-linkers, are provided. The materials are warmed up to an appropriate temperature for melting or thinning out the gel mixture, and are injected directly into the nuclear disc space through an intact annulus using a hypodermic needle. The gel mixture becomes solidified in the disc space after injection.

Inspection of the disc reveals that an appropriate level of augmentation may be obtained through either a single injection of material, or by multiple injections.

EXAMPLE 6

Elongated cylindrical plugs (0.5 mm to 5 mm in diameter, preferably 1 mm to 2 mm) of solid, porous, or fibrous collagen are provided in a dehydrated state. The plugs are compressed in the radial direction and are inserted into delivery cannula for delivery into disc space.

A guide wire or needle is used to penetrate the disc space through an intact annulus. A dilator is subsequently inserted into the disc space over the guide wire/needle, and the guide wire/needle is removed. The delivery cannula containing a collagen plug is attached to the dilator prior to extrusion of the plug into the disc space. As the plugs absorb moisture after entering the disc space, they become more compliant, flexible and expanded.

The level of disc augmentation achieved depends on the number of plugs inserted, and/or on the total plug volume deposited in the disc space.

EXAMPLE 7

Cylindrical plugs or rolls (2 mm-20 mm in diameter, preferably 10-15 mm) of solid, porous, or fibrous collagen are provided in a dehydrated state. The dehydrated plugs are typically more rigid than those in hydrated state, and thus, can be easily inserted into the disc space through an annular opening created by trauma or surgical incision.

Nucleotomy is necessary before the plug can be inserted. As the plugs absorb moisture after entering the disc space, they become more compliant, flexible and expanded.

The level of disc augmentation/replacement achieved depends on the size and number of plugs inserted into the disc space.

EXAMPLE 8

Particulate fascia used for cosmetic procedure (FASCIAN®) was modified to include a radiocontrast media. A small quantity of barium sulfate powder was blended with 80 mg of >0.5 mm Gastrocemius Fascia for visualization under fluoroscopic imaging. About 1-1.5 cc of water was added to the blend in the syringe for hydration.

After hydration for 5-10 minutes, the material (Fascian/Barium Sulfate/Water or F.B.W.) was injected into the nuclear disc space of a harvested porcine intervertebral disc. X-ray images of the disc were obtained before and after injection.

A small increase in disc height was noticed after injection. Also, manual compression indicated that the disc was stiffer after injection. The injected disc was also tested under compression up to 5000N. There was no gross leakage observed during the compression test. Only a slight oozing of a small amount of injected material was observed at the injection site, but it stopped quickly.

The disc was cut in the horizontal plane to confirm the location of the injected material. F.B.W. was found contained within the disc annulus and mixed in with nucleus pulposus.

EXAMPLE 9

Particulate fascia used for cosmetic procedures (FASCIAN®) was modified before experimentation to include a radiocontrast material. A small quantity of radio-contrast dye or barium sulfate powder was blended with about 200 mg of 0.25-1.0 mm Gastrocemius Fascia for visualization under fluoroscopic imaging. About 1.5-3 cc of saline was added to the blend in the syringe for hydration.

After hydration for about 30 minutes, the material (Fascian/Dye or Barium Sulfate/Water) was injected into the nuclear disc space of cadaveric intervertebral discs (L2-3 and L3-4). X-ray images of the discs were obtained before and after injection. A small increase in disc height was noticed radiographically after injection. There was no gross leakage observed at the injection site. In the case of L3-4 injection, the needle tip was maintained approximately at the center of the disc, which resulted in material deposition mainly within the nucleus pulposus.

EXAMPLE 10

Particulate fascia (FASCIAN®) having particle sizes of 0.25 mm and 0.5 mm was purchased from Fascia BioSystems. Collagen solutions were prepared, with each solution consisting of approximately 80 mg of particulate fascia, 0.75 ml of saline, and 0.25 ml HYPAQUE® radiocontrast solution.

Thoracic and lumbar discs in two pigs were subjected to stabbing injury. The injured discs were then injected with 1-2 ml of collagen solution at 4 weeks after injury. The injections were performed using a 3 ml syringe, a 20 gauge hypodermic needle and a graft placement device. Confirming X-ray was taken using C-arm fluoroscopy.

The injured discs appeared to have somewhat reduced heights at four weeks after injury. Of approximately 12 injected discs, there was only one leakage observed. The amount of leakage was visually estimated to be less than 20% of the total volume injected. The low incidence of leakage indicates that the annulus is capable of self-sealing when a small gauge needle is used for injection.

The disc height increased upon collagen injection depending on the injected volume. In particular, an approximately 46% increase in disc height was achieved with 2 ml injection. In some cases the disc height gain was reduced after injection as radio-contrast dye and water molecules diffused out of the disc under intra-discal pressure.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of augmenting an intervertebral disc, said method comprising surgically adding to the nucleus of an intervertebral disc an injectable material consisting essentially of small particles of natural tissue selected from the group consisting of intervertebral disc, fascia, ligament, tendon, skin, and other connective tissue.

2. The method of claim 1 wherein said surgically adding step comprises injecting small particles of natural tissue into the nucleus of an intervertebral disc.

3. The method of claim 1 wherein said small particles of natural tissue comprises particles ranging from 0.05 mm to 5 mm in size.

4. The method of claim 1 wherein said small particles of natural tissue comprises particles ranging from 0.05 mm to 3 mm in size.

5. The method of claim 1 wherein said small particles of natural tissue comprises particles ranging from 0.05 mm to 1 mm in size.

6. The method of claim 1 wherein said small particles of natural tissue comprises particles ranging from 0.25 mm to 1 mm in size.

7. The method of claim 1 wherein said small particles of natural tissue are injected in a dehydrated state.

8. The method of claim 1 wherein said small particles of natural tissue are injected in a non-dehydrated state.

9. The method of claim 8 wherein said small particles of natural tissue are injected as a gel.

10. The method of claim 8 wherein said small particles of natural tissue are injected as a solution or suspension.

11. The method of claim 1 wherein said small particles of natural tissue are provided as a formulation that additionally includes a cross-linking agent to promote crosslinking of collagen molecules contained in the small particles of natural tissue.

12. The method of claim 1 wherein said small particles of natural tissue are provided as a formulation that additionally includes a radio contrast media.

13. The method of claim 1 wherein said small particles of natural tissue are provided as a formulation that additionally includes an analgesic.

14. The method of claim 1 wherein said small particles of natural tissue are provided as a formulation that additionally includes an antibiotic.

15. The method of claim 1 wherein said small particles of natural tissue are provided as a formulation that additionally includes proteoglycans.

16. The method of claim 1 wherein said small particles of natural tissue are provided as a formulation that additionally includes growth factors.

17. The method of claim 1 wherein said small particles of natural tissue are provided as a formulation that additionally includes one or more other types of cells effective to promote healing, repair, regeneration and/or restoration of the disc, and/or to facilitate proper disc function.

* * * * *